US008579790B2

(12) United States Patent
Jeffery et al.

(10) Patent No.: US 8,579,790 B2
(45) Date of Patent: Nov. 12, 2013

(54) APICAL RING FOR VENTRICULAR ASSIST DEVICE

(75) Inventors: Brian D. Jeffery, Melvindale, MI (US); Sunil K. Dasara, Ann Arbor, MI (US)

(73) Assignee: Thoratec Corporation, Pleasanton, CA (US)

( * ) Notice: Subject to any disclaimer, the term of this patent is extended or adjusted under 35 U.S.C. 154(b) by 30 days.

(21) Appl. No.: 13/343,918

(22) Filed: Jan. 5, 2012

(65) Prior Publication Data

US 2013/0178694 A1    Jul. 11, 2013

(51) Int. Cl.
*A61N 1/362* (2006.01)

(52) U.S. Cl.
USPC .......................................................... 600/16

(58) Field of Classification Search
USPC .......................................................... 600/16
See application file for complete search history.

(56) References Cited

U.S. PATENT DOCUMENTS

| | | | |
|---|---|---|---|
| 1,093,868 A * | 4/1914 | Leighty ...................... | 285/334.1 |
| 4,790,843 A | 12/1988 | Carpentier et al. | |
| 5,354,331 A | 10/1994 | Schachar | |
| 5,504,978 A | 4/1996 | Meyer, III | |
| 5,824,069 A | 10/1998 | Lemole | |
| 6,143,025 A | 11/2000 | Stobie et al. | |
| 6,146,325 A | 11/2000 | Lewis et al. | |
| 6,319,231 B1 | 11/2001 | Andrulitis | |
| 6,458,163 B1 | 10/2002 | Slemker et al. | |
| 6,732,501 B2 | 5/2004 | Yu et al. | |
| 6,942,672 B2 | 9/2005 | Heilman et al. | |
| 7,048,681 B2 | 5/2006 | Tsubouchi et al. | |
| 2002/0058994 A1 | 5/2002 | Hill et al. | |
| 2002/0095210 A1 | 7/2002 | Finnegan et al. | |
| 2003/0023302 A1 | 1/2003 | Moe et al. | |
| 2004/0007515 A1 | 1/2004 | Geyer | |
| 2004/0015232 A1 | 1/2004 | Shu et al. | |
| 2004/0024285 A1 | 2/2004 | Muckter | |
| 2004/0030381 A1 | 2/2004 | Shu | |
| 2004/0171905 A1 | 9/2004 | Yu et al. | |
| 2004/0210305 A1 | 10/2004 | Shu et al. | |
| 2007/0134993 A1 | 6/2007 | Tamez et al. | |
| 2007/0213690 A1 | 9/2007 | Phillips et al. | |
| 2009/0171136 A1 | 7/2009 | Shambaugh, Jr. | |
| 2011/0118766 A1 | 5/2011 | Reichenbach et al. | |
| 2011/0118829 A1 | 5/2011 | Hoarau et al. | |
| 2011/0118833 A1 | 5/2011 | Reichenbach et al. | |

\* cited by examiner

*Primary Examiner* — George Manuel
(74) *Attorney, Agent, or Firm* — MacMillan, Sobanski & Todd, LLC

(57) ABSTRACT

An apical ring for coupling a conduit of a ventricular assist device to a heart has an annular disk with a central aperture for receiving the conduit. A collar is axially aligned with the central aperture and has a cylindrical shape interrupted by a gap between first and second ends of the collar. The collar has a fixed section joined to the annular disk and has a cantilever section extending from the fixed section to the first end of the collar. A tightener selectively drives the first end toward the second end to close the gap in order to retain the conduit within the collar. The cantilever section includes a relief slot that is expandable for extending a circumferential length of the cantilever section in response to interacting with the conduit when the gap is closed.

15 Claims, 7 Drawing Sheets

APICAL RING FOR VENTRICULAR ASSIST DEVICE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to cardiac assist systems, and, more specifically, to an apical ring that provides an attachment point to a patient's heart for clamping an inflow conduit of a pump and for receiving a plug if the pump is no longer needed.

A heart pump system known as a left ventricular assist system (LVAS) can provide long term patient support with an implantable pump associated with an externally-worn pump control unit and batteries. The LVAS improves circulation throughout the body by assisting the left side of the heart in pumping blood. One such system is the DuraHeart® LVAS system made by Terumo Heart, Inc., of Ann Arbor, Mich. A typical LVAS system employs a centrifugal pump, an inflow conduit coupling the pump to the left ventricle, and an outflow conduit coupling the pump to the aorta. The inflow conduit may be integrally formed with a pump housing. The inflow conduit connects to the heart via an attachment cuff. An example of an inflow conduit is shown in U.S. Pat. No. 7,048,681, incorporated by reference herein in its entirety.

The apical cuff or ring is the interface and mounting element for the pump and blood inflow tube (i.e., conduit) to the apex of the left ventricle of the heart. The assist device may be mounted to the heart through a process of elevating the left ventricle out of the pericardial sac, defibrillating the heart, suturing the ring at the apex, coring through the apex inside the ring, inserting the blood inflow conduit through the cored hole, and clamping the ring onto the conduit. Thus, the apical ring may perform the functions of 1) providing a suture attachment point onto the epicardium muscle, 2) sealing against potential blood leakage from the left ventricle around or outside of the inflow conduit, 3) permitting axial and/or or rotational adjustment of the pump and inflow conduit with respect to the left ventricle during implantation, and 4) fixing the inflow conduit in a final position with respect to the left ventricle.

The apical ring may preferably be provided with a clamping mechanism to fix the inflow conduit into its final position. Because an inflow conduit may typically include a sintered outside surface, there may be significant variation in the outside diameter of the inflow conduit from unit to unit in the region which is to be clamped by the apical ring. Consequently, conventional clamps have been made with an adjustable circumference in view of the variations in the inflow conduit.

Ease of assembly, efficient implantation, and consistency of results are important in the context of cardiac surgery. It would be desirable to provide for a clamping attachment of the inflow conduit with minimal or no adjustment, with low clamping effort, and with a small dimensional profile (i.e., footprint) of the clamp mechanism and ring once it is attached to the pump and the heart.

SUMMARY OF THE INVENTION

In one aspect of the invention, an apical ring is provided for coupling a conduit of a ventricular assist device to a heart. An annular disk has a central aperture for receiving the conduit. A collar is axially aligned with the central aperture and has a cylindrical shape interrupted by a gap between first and second ends of the collar. The collar has a fixed section joined to the annular disk and has a cantilever section extending from the fixed section to the first end of the collar. A tightener selectively drives the first end toward the second end to close the gap in order to retain the conduit within the collar. The cantilever section includes a relief slot that is expandable for extending a circumferential length of the cantilever section in response to interacting with the conduit when the gap is closed.

DETAILED DESCRIPTION OF PREFERRED EMBODIMENTS

Figure 1:
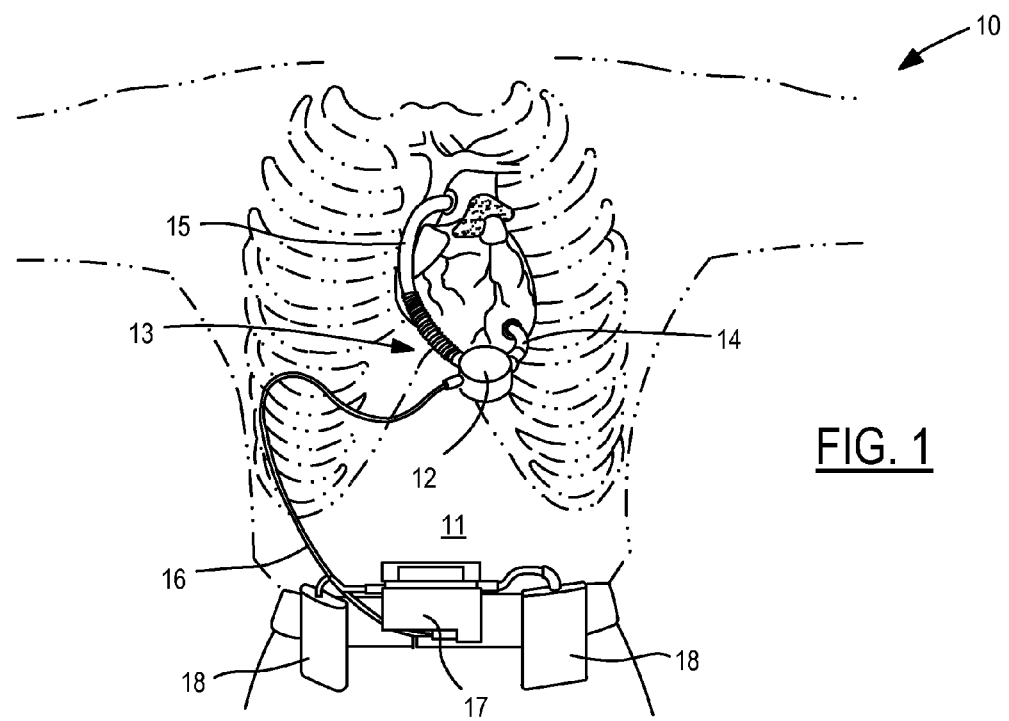
FIG. 1 is a front view of a left ventricular assist system having a pump implanted into a patient.

Referring to FIG. 1, a patient 10 is shown in fragmentary front elevational view. Surgically implanted into the patient's abdominal cavity 11 is the pumping portion 12 of a ventricular assist device 13. An inflow conduit 14 conveys blood from the patient's left ventricle into the pumping portion 12, and an outflow conduit 15 conveys blood from the pumping portion 12 to the patient's ascending thoracic aorta. A power cable 16 extends from the pumping portion 12 outwardly of the patient's body via an incision to a compact controller 17. A power source, such as battery packs 18, is worn on a belt about the patient's waist and connected with controller 17.

Each of the conduits 14 and 15 may include a tubular metallic housing proximate the pumping portion 12. At the end of inflow conduit 14 connected to the patient's heart (preferably at the apex of the left ventricle), and at the end of outflow conduit 15 connected to the ascending thoracic aorta, the conduits are generally attached to the natural tissue by sutures through the use of a sewing ring or cuff so that blood flow communication is established and maintained. The distal end of the inflow conduit 14 is inserted through the ventricle wall and into the heart in order to establish blood flow from the heart to the pumping portion 12.

Figure 2:
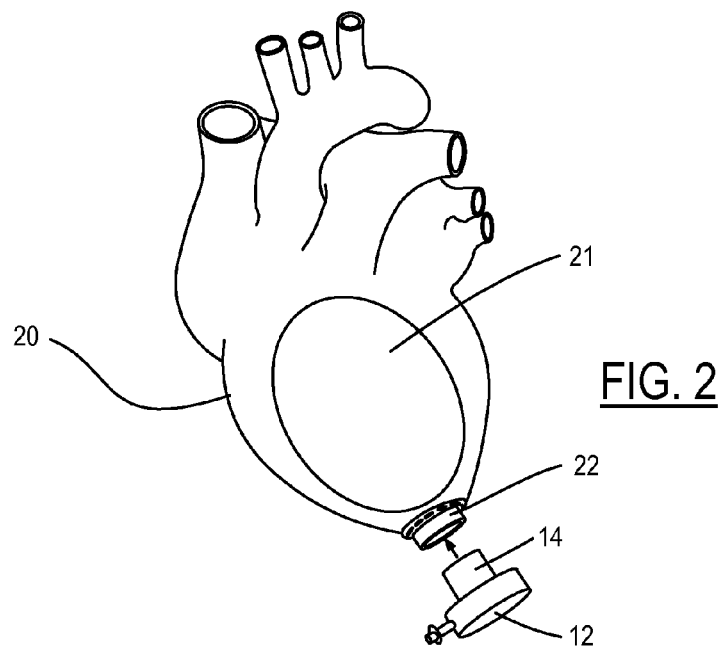
FIG. 2 is a perspective view showing the insertion of an inflow conduit through an apical ring into the left ventricle.

Inflow conduit 14 may be more preferably comprised of a rigid tube extending axially from the pump housing as shown in FIG. 2. This allows for a shorter inflow conduit and for a more compact placement. For both types of conduits, left ventricle 21 is accessed via apical ring or cuff 22 sutured to the apex of the heart and surrounding a section of heart tissue that is cored to provide a passage for conduit 14. The outer surface of conduit 14 preferably has a sintered coating in order to promote a stable blood surface and to facilitate sealing/coagulation between the outer diameter of conduit 14 and the ventricular wall. Apical ring 22 clamps onto the same sintered surface. Due to variations in the manufacturing process using sintering, the resulting tolerance range of the outer diameter creates a challenge for providing consistent clamping without requiring adjustments to be made by a surgeon during attachment.

A first embodiment of an apical ring for overcoming the foregoing problems is shown in FIGS. 3-11.

Figure 3:
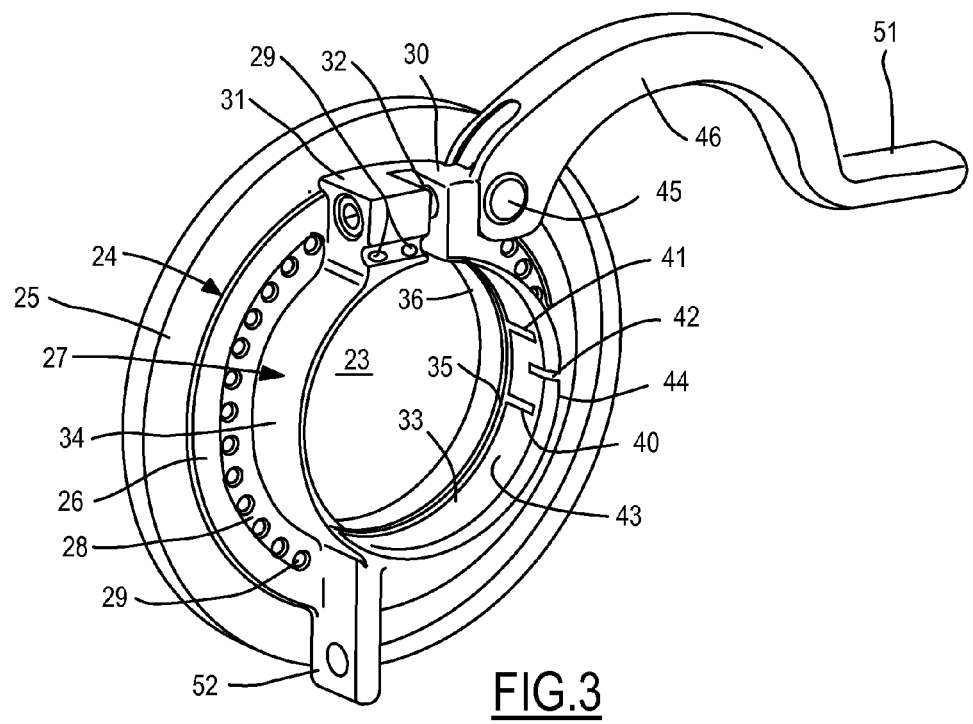
FIG. 3 is a left-side perspective view of an apical ring of the present invention in an open position.

Referring to FIG. 3, an apical ring 24 (preferably formed from a machined titanium alloy or other rigid material such as a biocompatible thermoplastic resin) may be associated with a sealing disk 25 that is sutured to and seals against the outer surface of the left ventricle. Ring 24 includes an annular disk 26 that is disposed against sealing disk 25. Ring 24 further includes a collar 27 aligned with a central aperture 23 of disk 26. Collar 27 has a substantially cylindrical shape interrupted by a gap 32 between a first end 30 and a second end 31. First and second ends 30 and 31 may preferably be formed as enlarged blocks as shown. Collar 27 has a fixed section 34 anchored to disk 26 and a cantilever section 33 extending from fixed section 34 but separated from disk 26 by a gap 35. By virtue of being suspended, cantilever section 33 provides an adjustable inside diameter in collar 27. The initially manufactured placement of cantilever section 33 provides an inside diameter sufficiently large to allow easy insertion of the inflow conduit. Cantilever section 33 is subsequently clamped to a lesser inside diameter in order to secure the inflow conduit.

Sealing disk 25 has an inner edge 36 that is coaxial with central aperture 23 of annular disk 26 and collar 27 and has an inside diameter selected to provide a good seal around the inflow conduit. Sealing disk 25 may preferably be comprised of a molded silicone body with a Dacron covering, for example. A first side of sealing disk 25 bears against annular disk 26 and a second side bears against the heart. Annular disk 26 includes a suturing flange 28 having a plurality of suturing holes 29 spaced around suturing flange 28 that may be formed within a trough in order to protect the sutures. Suturing holes 29 also pass through second end 31.

A tightener is provided for selectively driving first end 30 toward second end 31 to close gap 32 for retaining the conduit within collar 27 once it is placed in its final location. The tightener may be comprised of a C-clamp mechanism as shown in FIGS. 3-11.

The prior art has shown manually adjustable clamps that are operated by manual adjustment of a screw connection within the clamp. The present invention provides automatic adjustment of the clamp to the particular outside diameter for the particular inflow conduit being received. Cantilever section 33 includes relief slots 40, 41, and 42 penetrating first and second edges 43 and 44 of cantilever section 33. Relief slots 40-42 are expandable for extending the circumferential length of cantilever section 33 in response to interaction between the inflow conduit and the clamp when gap 32 is closed (e.g., in the manner of stretching of its length). More particularly, relief slots 40-42 act as a spring that is extendable around the inflow conduit when the conduit has some extra outer diameter to be accommodated. One or more relief slots can be used, and preferably at least one relief slot is provided in each circumferential edge 43 and 44. Each individual relief slot is not coaxial with any other relief slot (i.e., they are all offset as shown in FIG. 3).

Figure 4:
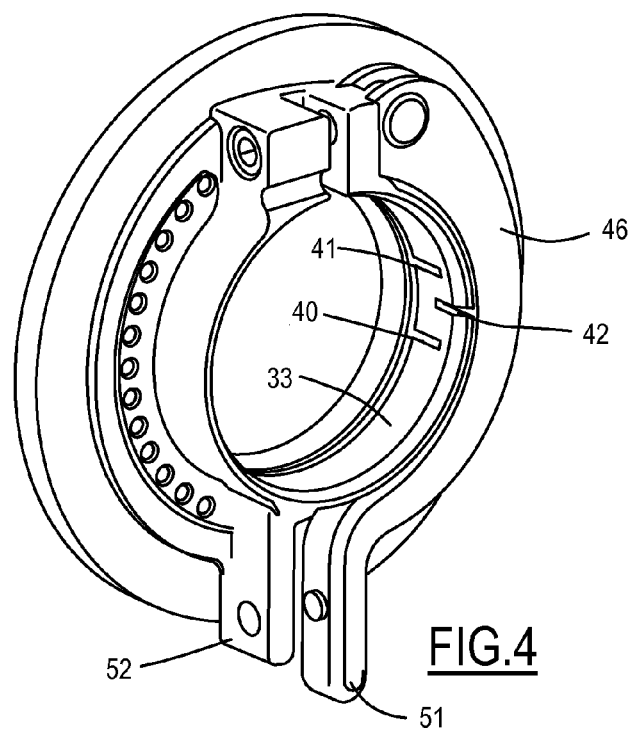
FIG. 4 is a left-side perspective view of the apical ring of FIG. 3 in a closed position.

The C-clamp of FIGS. 3-11 is comprised of a pivot pin 45 and a lever arm 46. Pivot pin 45 is disposed at a substantially fixed location with respect to annular disk 26 and is adjacent first end 30. As shown in the exploded view of FIG. 12, pivot pin 45 may be attached to second end 31 by a screw 47 that passes through first end 30 and is threaded through pivot pin 45. Thus, pivot pin 45 is maintained at a fixed distance from second end 31. Lever 46 has apertures 48 for receiving the ends of pivot pin 45, whereby lever 46 rotates on pivot pin 45 between an open position as shown in FIG. 3 and a closed position as shown in FIG. 4. Lever 46 has a cam surface 50 that is slidable against first end 30. Cam surface 50 has a variable profile extending to a gradually larger radius away from pivot pin 45 in order to progressively drive first end 31 toward second end 30 as lever 46 rotates from the open position to the closed position.

Referring again to FIG. 3, lever 46 has a push tab 51 at its end to allow a surgeon to easily press on the clamp to move it to the closed position. Annular disk 26 further includes a thumb tab 52 at a position diametrically opposite from first end 30 so that the surgeon can move the clamp to the closed position by pinching between tabs 51 and 52. FIG. 4 shows lever 46 moved to its closed position with tabs 51 and 52 brought face-to-face. In the event that the outer diameter of the inflow conduit is at the upper end of its tolerance range, reaching the closed position is achievable without requiring a screw adjustment. Closing effort remains small because relief slots 40-42 can spread slightly apart to provide the necessary increase of the circumferential length of cantilever section 33. The overall profile (i.e., size) of ring 24 in its closed position is relatively small and unobtrusive, thereby providing a compact and efficient system.

Figure 5:
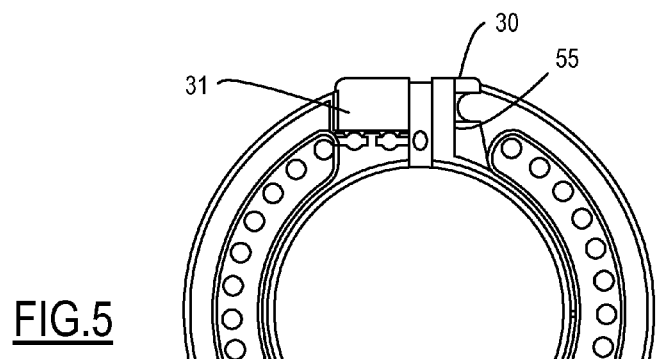
FIG. 5 is a front view of the apical ring of FIG. 3 with the clamp lever removed.
Figure 6:
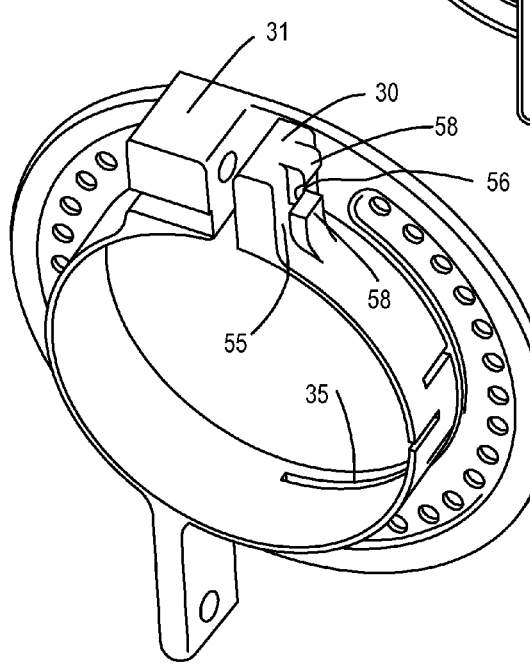
FIG. 6 is a right-side perspective view of the apical ring of FIG. 5.
Figure 7:
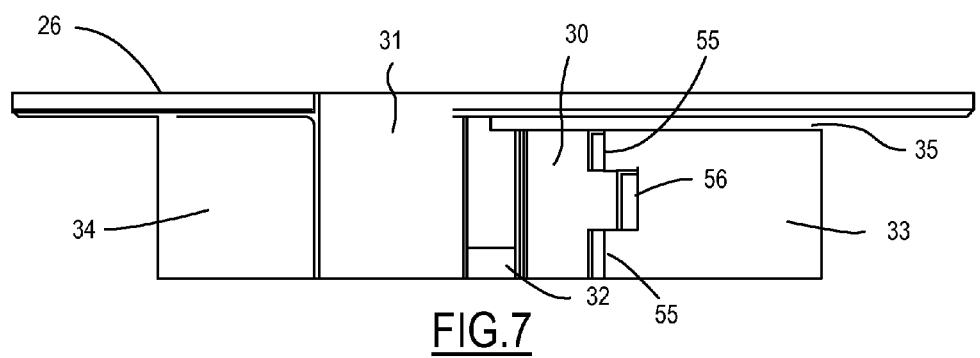
FIG. 7 is a top view of the apical ring of FIG. 5.
Figure 8:
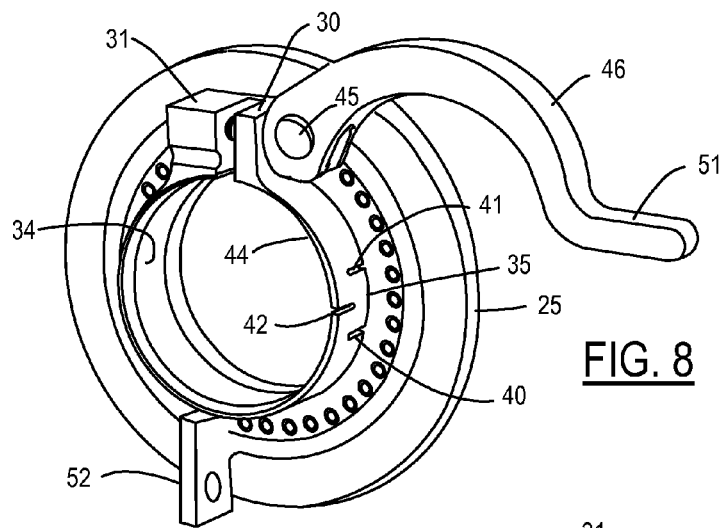
FIGS. 8 and 9 are right-side perspective views of the apical ring of FIG. 3 is the open and closed positions, respectively.
Figure 9:
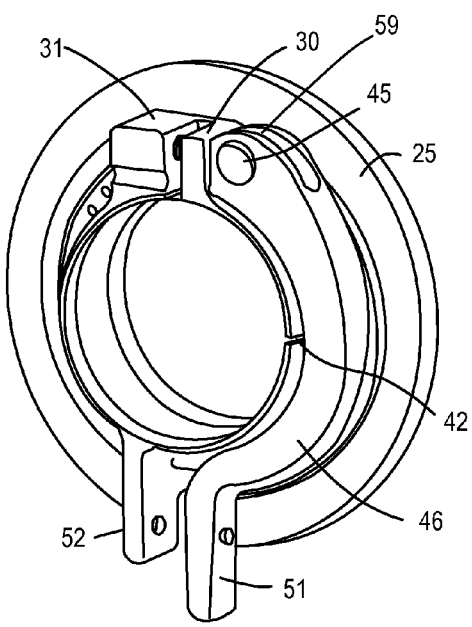

As shown in FIGS. 5 and 6, first end 30 may preferably include cam follower surface 55 alongside a groove 56 that receives pivot pin 45. As seen in FIG. 7, first end 30, cam follower surface 55, and groove 56 are movable toward second end 31 to close gap 32 by virtue of slit 35 between cantilever section 33 and annular disk 26. Protrusions 58 (FIG. 6) are received in a central groove 59 (FIG. 9) in lever 46, so that lever 46 is limited to moving in a plane that is parallel with annular disk 26.

Figure 10:
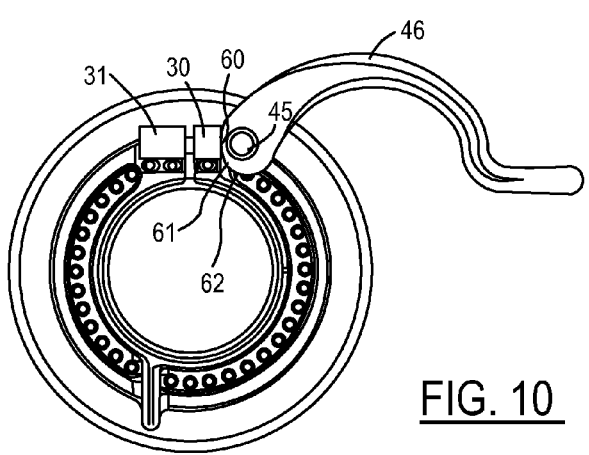
FIG. 10 is a front view of the apical ring in the open position.
Figure 11:
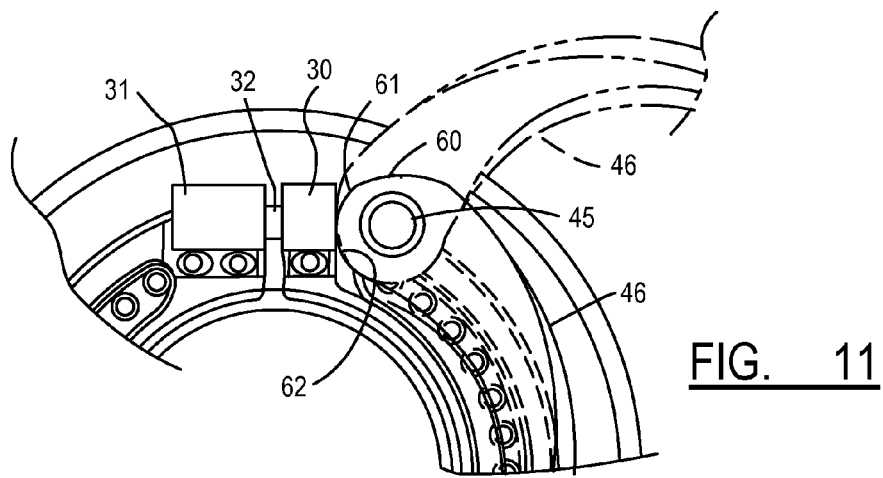
FIG. 11 is a front view showing the operation of the lever and the cam surface in greater detail.
Figure 12:
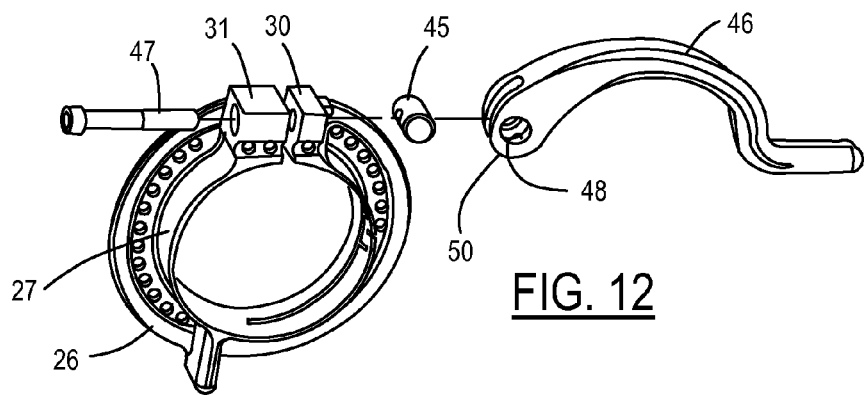
FIG. 12 is an exploded, perspective view showing an attachment of the lever.

As best seen in FIG. 10, cam surface 50 on lever 46 provides a minimum thickness section 60 and an increasing thickness section 61. Section 60 occupies the space between pivot pin 45 and first end 30 while in the open position as shown in FIG. 10. A substantially flat section 62 of cam surface 50 corresponds to the closed position of lever 46. Moving between the open and closed positions, cam section 61 progressively drives end 30 toward end 31. As shown in FIG. 11, the closed position shown in solid lines results with lever 46 in the closed position in which end 30 is forced toward end 31 so that gap 32 is reduced or eliminated.

Figure 13:
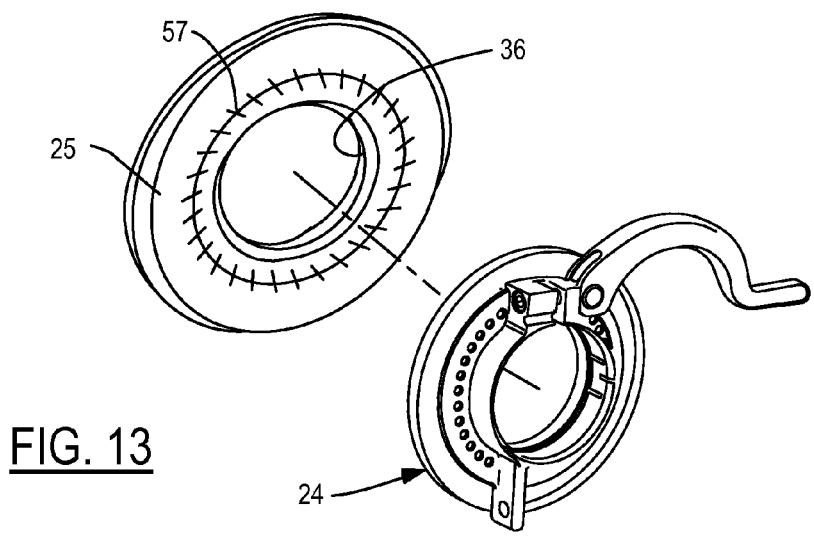
FIG. 13 is an exploded, perspective view showing the sealing disk with the apical ring.

FIG. 13 shows a sewing pattern 57 on sealing disk 25 during attachment by suturing to the heart.

Figure 14:
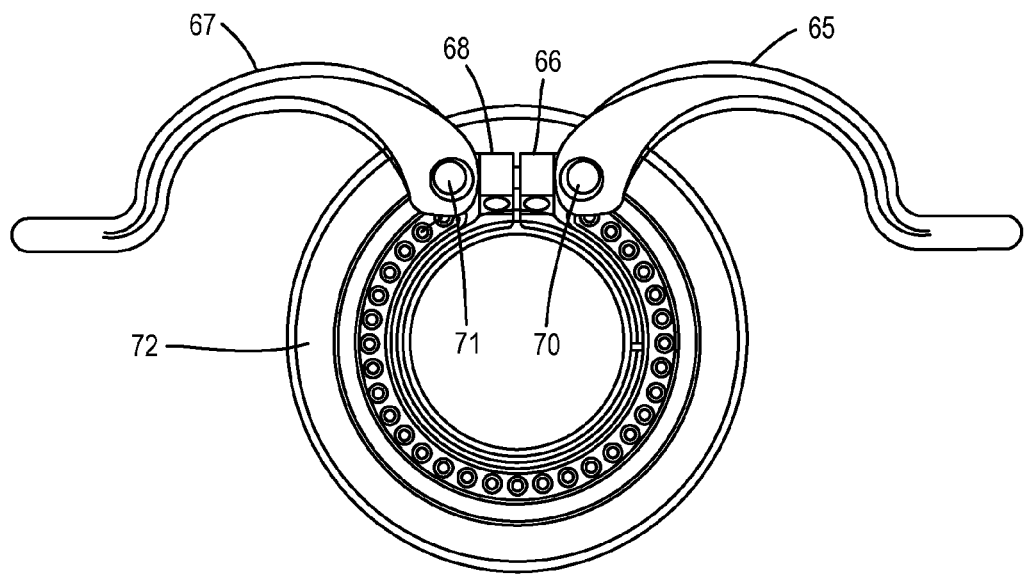
FIG. 14 is a front view showing an alternative embodiment with a pair of complementary levers.

An alternate embodiment shown in FIG. 14 employs a pair of opposed tightening clamps 65 and 67 disposed against collar ends 66 and 68. Ends 66 and 68 are preferably each suspended by corresponding cantilever sections of the collar. Levers 65 and 67 may be attached to pivot pins 70 and 71 that are formed as fixed posts on annular disk 72, for example. Alternatively, pivot pins 70 and 71 may be interconnected by a rod or shaft passing through corresponding holes in ends 66 and 68.

Figure 15:
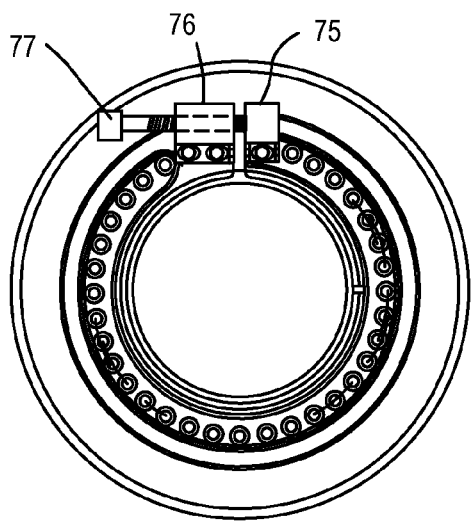
FIG. 15 is a front view showing an alternative embodiment with a screw adjustment.

In an alternative embodiment shown in FIG. 15, collar ends 75 and 76 may be tightened using a threaded screw 77. End 75 is suspended on a cantilever section. Relief slots in the collar (not shown) may be useful with this screw-type tightener to help ensure that a full tolerance range of conduit outer diameters can be easily accommodated. Other hose-clamp type tighteners can also be employed having relief slots.

Figure 16:
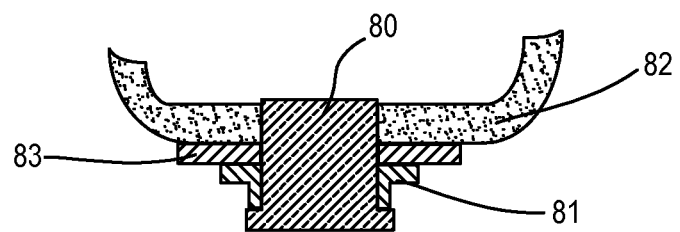
FIG. 16 is a cross section showing the apical ring being used to clamp a plug for sealing the site when the pump is no longer needed.

The present invention facilitates the releasing of the clamp in order to enable the adjustment of the position of the inflow conduit and pump as well as subsequent removal of the pump and/or inflow conduit for replacement with a different pump or inflow conduit. In the event of recovery of the natural pumping capacity of the heart, a plug 80 shown in FIG. 16 can be clamped into ring 81 so that it passes through myocardium 82 and sealing disk 83.

What is claimed is:

1. An apical ring for coupling a conduit of a ventricular assist device to a heart, comprising:
   an annular disk with a central aperture for receiving the conduit, wherein the annular disk is comprised of a suturing flange;
   a collar axially aligned with the central aperture and having a cylindrical shape interrupted by a gap between first and second ends of the collar, wherein the collar has a fixed section joined to the annular disk and has a cantilever section extending from the fixed section to the first end of the collar; and
   a tightener for selectively driving the first end toward the second end to close the gap in order to retain the conduit within the collar;
   wherein the cantilever section includes a relief slot that is expandable for extending a circumferential length of the cantilever section in response to interacting with the conduit when the gap is closed.

2. The apical ring of claim 1 wherein the relief slot penetrates an edge of the collar.

3. The apical ring of claim 1 wherein the cantilever section has a first circumferential edge and a second circumferential edge, and wherein the relief slot axially penetrates the first circumferential edge.

4. The apical ring of claim 3 further comprising a second relief slot axially penetrating the second circumferential edge, wherein the second relief slot is not coaxial with the relief slot penetrating the first circumferential edge.

5. The apical ring of claim 4 wherein the first circumferential edge is penetrated by a plurality of relief slots.

6. The apical ring of claim 1 wherein the tightener is comprised of:
   a pivot pin disposed at a substantially fixed location with respect to the annular disk and adjacent the first end of the collar; and
   a lever mounted to the pivot pin to rotate between an open position and a closed position, wherein the lever has a cam surface slidable against the first end to progressively drive the first end toward the second end as the lever rotates from the open position to the closed position.

7. The apical ring of claim 6 wherein the first end includes a protrusion, and wherein the lever includes a central groove receiving the protrusion so that the lever moves in a plane that is parallel to the annular disk.

8. The apical ring of claim 6 further comprising:
   a thumb tab projecting from the annular disk at a position diametrically opposite to the first end.

9. The apical ring of claim 6 wherein the pivot pin is coupled to the second end of the collar.

10. The apical ring of claim 1 wherein the collar has a second cantilever section extending from the fixed section to the second end.

11. The apical ring of claim 10 wherein the tightener is comprised of:
    a first pivot pin disposed at a first substantially fixed location with respect to the annular disk and adjacent the first end of the collar;
    a first lever mounted to the first pivot pin to rotate between a first open position and a first closed position, wherein the first lever has a first cam surface slidable against the first end to progressively drive the first end toward the second end as the first lever rotates from the first open position to the first closed position;
    a second pivot pin disposed at a second substantially fixed location with respect to the annular disk and adjacent the second end of the collar; and
    a second lever mounted to the second pivot pin to rotate between a second open position and a second closed position, wherein the second lever has a second cam surface slidable against the second end to progressively drive the second end toward the first end as the second lever rotates from the second open position to the second closed position.

12. The apical ring of claim 1 further comprising a sealing disk having an inner edge that is coaxial with the central aperture of the annular disk and is sized to provide a seal around the conduit, wherein the sealing disk has a first side bearing against the suturing flange and a second side for bearing against the heart.

13. The apical ring of claim 1 wherein the annular disk and the collar are integrally formed.

14. The apical ring of claim 13 wherein the annular disk and the collar are comprised of titanium alloy.

15. An apical ring for coupling a conduit of a ventricular assist device to a heart, comprising:
    an annular disk with a central aperture for receiving the conduit;
    a collar axially aligned with the central aperture and having a cylindrical shape interrupted by a gap between first and second ends of the collar, wherein the collar has a fixed section joined to the annular disk and has a cantilever section extending from the fixed section to the first end of the collar, wherein the collar has a second cantilever section extending from the fixed section to the second end; and
    a tightener for selectively driving the first end toward the second end to close the gap in order to retain the conduit within the collar;
    wherein the cantilever section includes a relief slot that is expandable for extending a circumferential length of the cantilever section in response to interacting with the conduit when the gap is closed; and
    wherein the tightener is comprised of:
    a first pivot pin disposed at a first substantially fixed location with respect to the annular disk and adjacent the first end of the collar;

a first lever mounted to the first pivot pin to rotate between a first open position and a first closed position, wherein the first lever has a first cam surface slidable against the first end to progressively drive the first end toward the second end as the first lever rotates from the first open position to the first closed position;

a second pivot pin disposed at a second substantially fixed location with respect to the annular disk and adjacent the second end of the collar; and a second lever mounted to the second pivot pin to rotate between a second open position and a second closed position, wherein the second lever has a second cam surface slidable against the second end to progressively drive the second end toward the first end as the second lever rotates from the second open position to the second closed position.

\* \* \* \* \*